US007008931B2

(12) United States Patent
Yvin et al.

(10) Patent No.: US 7,008,931 B2
(45) Date of Patent: Mar. 7, 2006

(54) ANTI-INFLAMMATORY AND HEALING MEDICINE BASED ON LAMINARIN SULPHATE

(75) Inventors: Jean-Claude Yvin, Saint-Malo (FR); Susanne Alban, Regensburg (DE); Gerhard Franz, Regensburg (DE)

(73) Assignee: Laboratoires GOEMAR S.A., Saint-Malo Cedex (FR)

( * ) Notice: Subject to any disclaimer, the term of this patent is extended or adjusted under 35 U.S.C. 154(b) by 0 days.

(21) Appl. No.: 10/415,635

(22) PCT Filed: Nov. 2, 2001

(86) PCT No.: PCT/FR01/03397

§ 371 (c)(1),
(2), (4) Date: Jan. 29, 2004

(87) PCT Pub. No.: WO02/36132

PCT Pub. Date: May 10, 2002

(65) Prior Publication Data

US 2004/0127457 A1 Jul. 1, 2004

(30) Foreign Application Priority Data

Nov. 3, 2000 (FR) .................................. 00 14118

(51) Int. Cl.
*A01K 43/04* (2006.01)
(52) U.S. Cl. ........................................................ 514/54
(58) Field of Classification Search .................. 514/54
See application file for complete search history.

(56) References Cited

U.S. PATENT DOCUMENTS

| 3,200,110 A | * | 8/1965 | Gollin et al. ............... 536/18.5 |
| 5,135,920 A | | 8/1992 | Kanamaru et al. |
| 6,190,875 B1 | * | 2/2001 | Ben-Artzi et al. ............ 435/18 |

FOREIGN PATENT DOCUMENTS

| JP | 49130478 | 12/1974 |
| WO | WO 95/24907 | 9/1995 |

OTHER PUBLICATIONS

Vlodavsky et al. "Inhibition of tumor metastasis by heparanase inhibiting species of heparin," Invasion Metastasis, 1994-95, vol. 14, pp. 290-302.*
Hershkoviz et al. "Differential effects of polysulfated polysaccharide on experimental encephalomyelitis, proliferation of autoimmune T cells, and inhibition of heparanase activity," Journal of autoimmunity (1995) vol. 8, pp. 741-750.*
Bohn, J.A. et al., "(1-3)-β-D-Glucans as Biological Response modifiers: a review of structure-functional activity relationships", *Carbohydr. Polym.* (1995), vol. 28, pp. 3-14.
Cirellis, Al. F. et al., "Effect of sulfation on the biological activity of β-(1-3)-glucans from the tree fungus *Cyttaňa harioti* Fischer", Carbohydr. Res., vol. 190, (1989), pp. 329-337.
Paper D H, "Natural Products As Angiogenesis Inhibitors", *Planta Medica*, 1998, Vol. 64, No. 8, pp. 686-695 (XP002176352).
Hoffman R et al., "Inhibition of Angiogenesis and Murine Tumour Growth by Laminarin Sulphate", *British Journal of Cancer*;1996, vol. 73, No. 10, pp. 1183-1186.
Yoshido, Tomoaki et al, "A Liquid-Phase Binding Analysis for L-Selectin", *Eur. J. Biochem*, 1994, vol. 222(2), pp. 703-709 (XP001016234).
Xie X et al., "Inhibition of Selectin-Mediated Cell Adhesion and Prevention of Acute Inflammation by Monanticoagulant Sulfated Saccharides Studies With Carboxy-Reduced and Sulfated Heparin and With Trestatin A Sulfate", *J. Biological Chemistry*, American Society of Biological Chemists, 2000, Vo. 275, No. 44, pp. 34818-34825 (XP001031395).
Suzuki, et al., "Preparation and Biological Activities of Sulphated Derivatives of (1.fwdarw. 3)- .beta- D-Glucans", *J. Pharmacobio-Dyn.*, 1991, vol. 14(5), pp. 256-266.
Database CA., "Polysaccharide Sulfuric Acid Esters", *Chemical Abstracts Service*, Columbus, Ohio, retrieved from STN Database Accession No. 83:12692 XP002176355 & JP 49 130478 A (Ajinomoto Co., Inc.) Dec. 13, 1974.
Database CA, "Veterinary-Clincal Uses of Curdian Sulfate", *Chemical Abstracts Service*, Columbus, Ohio, retrieved from STN Database Accession No. 132:73593 XP002176356 A (Kichin, Kitosan Kenkyu) 1999, pp. 166-167.
Database Phin, "Goemar Expects French Approval for GL 32", *Agrow Newsletter*, 2000, No. 352, p. 22 (XP002176357).

* cited by examiner

*Primary Examiner*—James O. Wilson
*Assistant Examiner*—Jason H. Johnsen
(74) *Attorney, Agent, or Firm*—McDonnell Boehnen Hulbert & Berghoff LLP

(57) ABSTRACT

The invention concerns the use for preparing a medicine for treating inflammatory diseases induced by non-specific inflammatory responses, that is antigen-independent, of a laminarin sulphate, having a degree of sulphation not less than 1.9 and preferably between 2 and 2.5 degree of polymerization identical to that of the natural molecule, that is 20 to 30.

12 Claims, 3 Drawing Sheets

ANTI-INFLAMMATORY AND HEALING MEDICINE BASED ON LAMINARIN SULPHATE

PRIOR RELATED APPLICATIONS

The present application is a U.S. national phase application of PCT/FR01/03397, filed Nov. 2, 2001, which claims priority to French patent application 00/14118 filed Nov. 3, 2000.

The problems related to the treatment of inflammatory diseases which correspond to non-specific inflammatory reactions are far from being cleared up. As a matter of fact, the totality of the medicines proposed in that respect up to now present side-effects which limit their use. Among these medicines, the physician often has recourse to corticosteroids or to non-steroidic anti-inflammatory agents (AINS) whose efficiency is very often spectacular but whose drawbacks and whose bad compliance limit the use. The said drawbacks frequently find expression as far as the corticosteroids used by the general route are concerned through metabolic, endocrinal and digestive troubles as well as by the reawakening of infections. By the local route the corticoids may induce dermatoses or present a start again effect when terminating the treatment as well as a development of the infections. As far as the AINS are concerned, it happens when they are used by local route, that there occur erythemateous cutaneous reactions, local allergical reactions of the eczema type and, when they are used by general route, that there occurs digestive disorders, pruritus or itching and cutaneous eruptions.

By way of consequence, there is a permanent need to increase the number of these medicines, if possible by way of products which are at least as efficient as the corticosteroids but which do not present, as far as possible, the drawbacks of the latter.

This is the object contemplated by the applicant Company.

The applicant Company has the merit of having found that surprisingly and unexpectedly a particular sulfated polysaccharide satisfies the said need, i.e. laminarin sulfate which will be hereafter defined and for which other pharmacological activities are known which are disclosed in the following articles:

"*Inhibition of heparanase activity and tumor metastasis by laminarin sulfate and synthetic phosphorothioate oligodeoxynucleotides,* published by Miao-HQ; Elkin-M, Aingom-E, Ishai-Michaeli-R; Stain-Ca; Vlodasky-I in Int-J-Cancer 1999 Oct. 29 83: (3) 424–31, according to which the results as obtained underline the implication of heparanase in metastases as well as the potential clinical uses of various molecules inhibiting heparanase such as sulfated polysaccharides;

"*Inhibition of angiogenesis and murine tumour growth by laminarin sulphate*" published by Hoffman-R; Paper-DH; Donaldson-J; Vogl-H in Br-J-Cancer. 1996 May; 73(10) 1183–6, according to which a polysulfated glucane derivative slows down the growth of the murine tumour RIF-1 from 2 to 6 days;

"*Differential effects of polysulfates polysaccharide on experimental encephalomyelitis, proliferation of autoimmune T cells, and inhibition of heparanase activity*" published by Hershkoviz-R; Mor-F; Miao-HQ; Vlodavsky-I; Lider-O in J-Auto-immun 1995 October; 8 (5): 741–50 and according to which polysulfated polysaccharides may have potential clinical uses in the treatment of auto-immune diseases;

"*Characterisation of a laminarin sulphate which inhibits basic fibroblast growth binding and endothelial cell proliferation*" published by Hoffman-R; Paper-DH; Donaldson-J; Alban-S; Franz-G in J-Cell-Sci 1995 November; 108 (Pt 11): 3591–8 and according to which highly sulphated laminarin can be of interest against diseases associated with a depending cellular proliferation bFGF;

"*Laminarin sulfate mimics the effects of heparin on smooth muscle cell proliferation and basic fibroblast growth factor-receptor binding and mitogenic activity*" published by Mia-HQ; Ishai-Michaeli-R; Peretz-T; Vlodavsky-I in J-Cell-Physiol. 1995 September; 164 (3): 482–90 and according to which laminarin sulphate may have potential clinical uses in various situations such as the healing of wounds, angiogenesis and atherosclerosis;

"*Synthesis of laminarin sulfates with anticoagulant activity*" published by Alban S, Kraus J, and Franz G. in Arzneimittel-Forsch/drug res (1992) 42; 1005–1008;

"*Effects of laminarin sulphate on experimental atherosclerosis and on serum lipids in rabbits during long-term intermittent cholesterol feeding*" published by Besterman-EM in Atherosclerosis 1970 July–August; 12(1): 85–96;

"*Natural product as Angiogenesis Inhibitors*" published by Dietrich H. Paper in Planta Medica (December 1998) vol. 64, no. 8 pp. 686–695, according to which a highly sulphated β-(1,3) glucan obtained by sulphation of laminarin inhibits angiogenesis and presents an anti-tumoral activity against the RIF-1 tumor.

Laminarin is marketed by the Applicant Company under the trademark "PHYCARINE".

Consequently the subject of the invention is the use, for the preparation of a medicine for the treatment of inflammatory diseases coming from non specific inflammatory, in other words antigen independent reactions, of a particular sulphated polysaccharide, i.e. laminarin sulphate whose degree of sulphation is higher or equal to 1.9 and preferably from 2 to 2.5 and whose degree of polymerization, identical to that of the natural molecule is from 20 to 30 preferably from 23 to 25.

From a more general standpoint of view the invention relates to a medicine for the treatment of inflammatory diseases originating from non specific inflammatory in other words antigen-independent reactions, the said medicine comprising as its active substance an efficient concentration of a particular sulphated polysaccharide, i.e. laminarin sulphate, whose degree of sulphation is higher or equal to 1.9 and preferably from 2 to 2.5 and whose degree of polymerization, which is identical to that of the natural molecule, is from 20 to 30 preferably from 23 to 25.

The laminarin sulphate used according to the invention presents in the case of inflammatory diseases originating from non-specific in other words antigen-independent reactions, an anti inflammatory activity which can be compared to that of indometacin but which occurs at molecular concentrations which are clearly lower; moreover, it is not cytotoxic at the highest concentrations used and its anticoagulant activity is sufficiently weak, compared with that of heparin, for not being a drawback within the use according to the invention.

According to an advantageous embodiment of the use according to the invention, laminarin sulphate is used through pharmaceutical forms which are adapted to administration through the local or general route and more particularly 1. through cutaneous administration in the form of, especially, emulsions, ointments, gels and transdermic devices, 2. through rectal administration in the form of, especially, suppositories and rectal injections,
3. through parenteral administration in the form, especially, of injectable solutions (subcutaneous, intra articular, intra venous)
4. through oral administration in the form, especially, of tablets, syrups, drinkable solutions or suspensions, capsules, hard capsules, sachets,
5. through pulmonary administration, especially, in the form of aerosols.

The concentration of the active substance, especially the efficient concentration in the case of the above cited pharmaceutical forms, is selected in such a way that it makes possible the daily administration, in one or several times, of an amount of active substance per kg of the weight of the body of the patient from 2 to 40 mg/kg/day preferably from 10 to 25 mg/kg/day in the case of the oral administration and from 1 to 100 mg/kg/day, preferably from 10 to 30 mg/kg/day in the case of an administration through a pharmacological form for local use.

Hereafter there is a first disclosed a method for the preparation of laminarin sulphate and then the experiments which were performed in order to determine the activities in vitro and the anti-inflammatory activity in vivo of laminarin sulphate.

I—Preparation of Laminarin Sulphate

For the preparation of laminarin sulphate, laminarin is first extracted from a raw material consisting of brown algae and then the sulphation of the thus extracted laminarin is carried out.

The extraction of the laminarin can be performed using the method disclosed in the French Patent FR 92 08387. The sulphation of the laminarin can be carried out by way of the method disclosed in the following publication: Alban S, Kraus J., Franz G.: Synthesis of laminarin sulfates with anticoagulant activity, Arzneim-Forsch/drug Res (1992) 42; 1005–1008.

An improved method for the sulphation of laminarin is disclosed in the thesis of Susanne Alban, presented in 1993 at the University of Regensburg under the title "Synthese and physiologische Testung neuartiger Heparinoide".

Another improved method is disclosed in the thesis of Helmut Stibich, presented at the University of Regensburg in 2001 under the title "Neuartige, antiphologistisch wirksame (β(1-3)-Glucansulfate: Partialsynthese and physiologische Testung".

These methods enable to obtain a highly substituted laminarin sulphate, without degradation and with a good reproducibility under good conditions from the economical point of view, while remaining simple.

In order to obtain an efficient sulphation without degradation of the polysaccharidic chains, the sulphation reaction must be carried out under conditions which correspond to an absolute absence of water.

Before the sulphation, the laminarin is dried, for example on phosphorpentoxide ($P_2O_5$) and then dissolved in dymethylformamid or DMF. Due to its alternative effects on the polysaccharide, the DMF has an activating influence on the substitution. As a matter of fact, the association of the polar DMF with the OH groups leads to the cleavage of the intra and intermolecular hydrogen bonds or bindings and to the disintegration of the superior structures.

In order to carry out the sulphation reaction, it is possible to use advantageously the pyridine-$SO_3$ complex.

Due to the coordination of the electron-acceptor $SO_3$ with the electron-donor pyridine, the reactivity of $SO_3$ which is difficult to be controlled and which give raise to highly exothermic reactions which lead to degradations, is reduced. The pyridine-$SO_3$ complex presents with respect to other complexes the advantage of being neither too reactive nor too stable in other words too slow from the point of view of the reaction.

Due to the fact that the sulphation degree which is obtained is proportional to the molar excess in sulphation reagent and due to the fact that it is intended to obtain a degree of substitution higher than 2, it is advantageous to use a concentration of 6 moles of pyridine-$SO_3$ per mole of glucose.

In order to warrant the absence of water, it is possible to work under an atmosphere consisting of argon.

Furthermore, pyridine is added to the sulphation reagent in equimolar amount from the beginning of the reaction in order to directly collect the sulfuric acid which might be formed by the reaction of the $SO_3$-pyridine complex with water. The concentration of laminarin as well as that of the sulphation reagent must be as high as possible due to the fact that the solubility of the polysaccharide and that of the sulphation reagent are limited. In order to avoid at the beginning of the reaction a cooling of the mixture which could lead to solubility problems and in order to obtain an as regular as possible substitution, the solution of the $SO_3$-pyridne complex in DMF may be added not in one time but continuously during four hours.

The sulphation reaction can be carried out at a temperature from 20 to 60° C., preferably at about 40° C. Higher temperatures lead to a more efficient substitution but also to a degradation of the chains.

After the addition of the sulphation reagent, stirring is maintained during 6 hours at 60° C. At that temperature, a supplemental substitution occurs without degradation of the chains.

The supernatant of the mixture is separated by decantation. The residue is dissolved in 2.5 M of NaOH and then mixed with 10 times its volume of ethanol of 99%. The precipitate which forms at a temperature of 4–8° C. during the night is separated and then dissolved in diluted sodium hydroxide (solution having a pH of about 9). The solution is dialyzed in order to remove the salts and the molecules of low molecular weight using a membrane of the Spectrapor type whose cleavage threshold is 1,000 D and then brought to a pH of 7.0 by addition of NaOH and then lyophilized. The resulting laminarin sulphate is present in the form of sodium salt.

The molecular weight of the macromolecule is determined as hydrodynamic volume by gel chromatography using the system called "Fast Protein Liquid Chromatography" or FPLC marketed by the Company Pharmacia. The detection of the elution profile (eluant agent: 0.1M NaCL with 0.05% of sodium azIde, 30 ml/h) using a device known under the trademark Superdex 75HR10/30 (range of separation 3–70 kD) is carried out by measuring the refraction index. The laminarin sulphate corresponds to a narrow symmetric peak; the width of this peak is the same in the case of unsulphated laminarin and in the case of sulphated laminarin which constitutes the proof of the fact that the length of the chain remains the same. The relative molecular weight is determined using a standard curve and using pullulans (standard polymer: 5,800–853,000 D, Polymer Laboratories, separation Science Division). Due to the presence of the highly hydrated sulphate groups, the hydrodynamic volume is higher than the real molecular weight.

The degree of sulphation is determined by conductimetric titration of the free acid of the sulphated polysaccharide using 0.1 N NaOH, or by ionic chromatography after hydrolysis using a system HPLC. The first method presents the advantage of being also adapted to studies concerning the stability of NaOH increases when the sulphate groups are eliminated) while the HPLC method needs less substance and can be automated. As a control, it is possible to determine the sulphur content by elementary analysis.

It is further possible to control the homogeneity of the sulphation and the repartition of the sulphate groups on the different positions within the glucose molecule by a modified form of the methylation analysis followed by an examination called GC-MS (i.e. Gas Chromatography, Mass Spectrometry). The sulphation is practically total, which means that almost all the hydroxyl groups in the 6 position are sulphated. During the substitution of the secondary OH groups, there is no significant difference between the sulphation of the groups in the 2 position and of those in the 4 position.

The sulphation degree obtained proceeding as here above indicated is higher than 1.9 and more precisely from 2 to 2.5.

The degree of polymerization of the thus obtained laminarin sulphate is from 20 to 30, more precisely from 23 to 25.

The anti-inflammatory activity of the laminarin sulphate appears from the hereafter described three in vitro tests and the hereafter described in vivo test.

II In Vitro Examination of the Anti-Inflammatory Activity of Laminarin Sulphate

The three in vitro tests hereafter described respectively show that laminarin sulphate: inhibits the activation of the complement, which is an important process occurring at the beginning of the inflammatory phenomena (test 1); inhibits the chemiotaxy of the neutrophil polynuclears, cells which are characteristic of the infiltrate in the acute inflammatory reaction (test 2); and, inhibits the adhesion of the cells induced by the selectins L and P (test 3).

In a supplementary test (test 4), the anticoagulant activities of laminarin sulphate and of heparin are compared.

The three above said tests show that at three different steps of the inflammatory reaction laminarin sulphate presents an inhibiting action in a much more important manner than heparin which has not been divided into fractions, for example the heparin which is marketed by the company SIGMA under the designation "sodic heparin", obtained starting from the mucosal membrane of the pig intestine; that heparin constitutes the polysaccharide of reference.

Furthermore, compared with that of that heparin, the anticoagulant activity of laminarin sulphate is clearly lower (test 4). Consequently, in the case of laminarin sulphate, the ratio profit/risk is clearly higher than that of heparin.

Test 1: Measuring of the Anti-Complementary Activity

The complement system plays a key role in the inflammatory processes induced by infections. The substances which inhibit in vitro the activation of the complement are potentially in vivo anti-inflammatory products.

The activation of the complement can be carried out by the classical route in which the system antigen-antibody plays a role, or by the so-called alternative route. The anti-complementary activity of laminarin sulphate has been examined in vitro in comparison to that of the above heparin of low molecular weight used as reference (HBPM).

The evaluation of the anti-complementary reactivity is carried out by photometric or colorimetric measurement of the hemoglobin freed by lysis of the erythrocytes. The erythrocytes used are sheep antibody-sensitized erythrocytes for the classical route and rabbit erythrocytes for the altern route.

In a first step, the product to be tested and the complement system (obtained from human serum) are put into contact with one another and if necessary incubated during 30 minutes and then, in a second step, they are put into contact with the erythrocytes during 45 minutes.

The more the test product inhibits the complement, the more the lysis of the erythrocytes is weak and the less the amount of freed hemoglobin is important.

The anti-complementary activity is expressed in IC (50) (IC meaning "inhibiting concentration") which designates the concentration expressed in Hg of test substance per ml of mixture of the test substance and the serum ($\mu$g/ml), concentration which is necessary to inhibit by 50% the activity of the complement.

Figure 1:
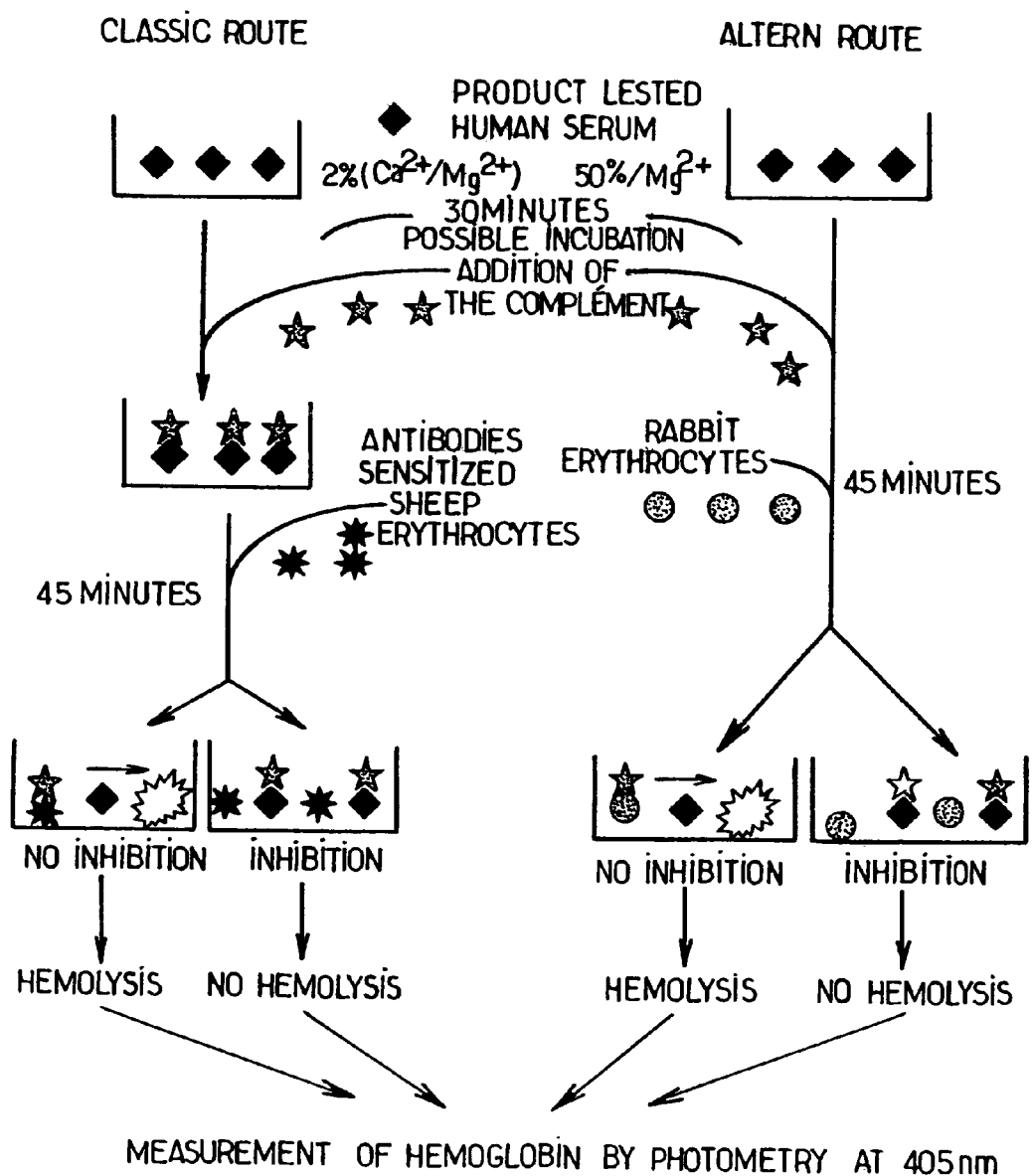
FIG. 1 shows a reaction diagram illustrating the various steps of the test of inhibition of the complement activation.

FIG. 1 shows a reaction diagram illustrating the various steps of the test which has been described.

The results as obtained show that: in connection with the inhibition of the activation of the complement by the classical way the value of the IC (50) as far as laminarin sulphate is concerned is 0.54±0.06 $\mu$g/ml, and as far as heparin is concerned it is 43.7±1.9; therefore it appears that when used by the classical route, laminarin sulphate is 80 times more active on the inhibition of the complement than heparin; in connection with the inhibition by the alternative route, the value of IC (50) as far as the laminarin sulphate (without incubation) is concerned, is 43 $\mu$g/ml and that of heparin is 464 $\mu$g/ml; consequently in the alternative route laminarin sulphate is 10 times more active on the inhibition of the complement than heparin; laminarin sulphate prevents the consumption of the complement; as a matter of fact it is known that generally, as soon as the serum is thawed, the activation of the complement starts; however the proteins of the complement are stable only during a limited time due to the inhibition by endogenous inhibitors due to which, there occurs generally a loss of the complementary reactivity; however a prolongation of the activity of the complement of more than 100% was observed for laminarin sulphate in the activation by the alternative route provided the laminarin sulphate is introduced at low concentrations (the said prolongation being of 50% for a dose of 2.4 $\mu$g/ml) which permits to come to the conclusion according to which laminarin sulphate prevents the consumption of the complement.

By way of consequence, laminarin sulphate not only blocks the activation of the complement induced in the test but also inhibits its spontaneous activation.

Test 2: Examination of the Influence on the Chemiotaxy of the Granulocytes

The polymorphnuclear neutrophiles or PMN are cells which are characteristic of the infiltrate of the acute inflammation. The movement or the migration of neutrophiles from inside of the blood vessels in direction of the tissues is provoked by molecules which are called chemotaxins. Two chemotaxins are particularly important in the case of the polynuclear neutrophiles, i.e. the fragment C5a of the complement and the interleukin 8 (IL-8). The movement of the neutrophiles can be aleatory (which means that a so called chemokinesis occurs) or can be oriented along the length of a gradient of chemotaxins.

It is known that molecules which are liable to inhibit that migration of the neutrophiles can be used in the prevention of the induction of the inflammatory response.

Figure 2:
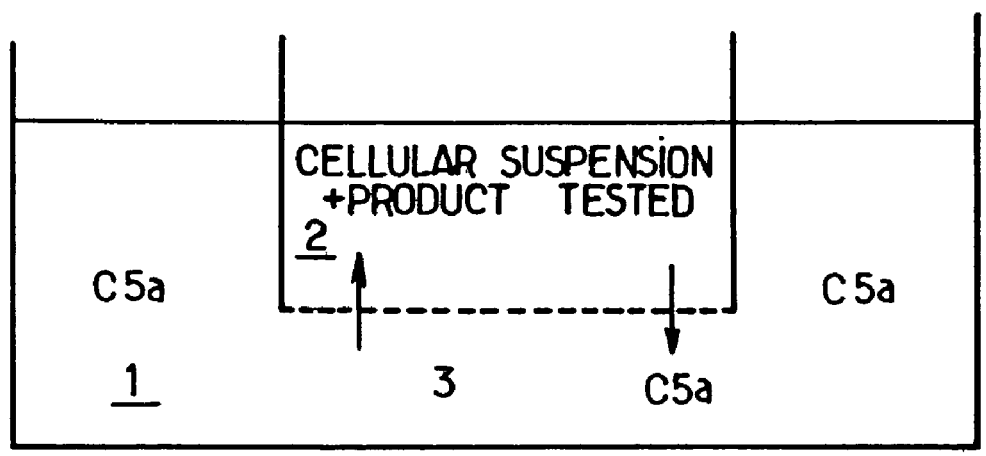
FIG. 2 is a schematically view of the Boyden Chamber.

Consequently, the ability of laminarin sulphate to inhibit the chemotaxy of laminarin sulphate was examined; this study has been carried out in vitro by way of the test called Test of the Boyden Chamber (a variant of the Boyden Chamber having 96 holes was used) the fragment C5a in the form of human serum activated with Zymosan having been used as chemiotaxin. As shown on FIG. 2, the Boyden Chamber comprises 2 compartments respectively 1 and 2 which are separated by a membrane 3 consisting of polycarbonate (dimension of the pores 3 $\mu$m). The pores of the said membrane authorize the active passing of the cells but not their passive diffusion.

The polymorphnuclear neutrophiles PMN are placed in the higher compartment 2 together with the substance to be tested at various doses. The C5a is placed in the lower compartment. With the time, the C5a diffuses in the higher or superior compartment and the PN actively migrate through the membrane into the lower compartment.

The measurement of the inhibition of the chemotaxy is carried out by numbering the cells which have been attracted in the lower compartment. For the numbering of the cells, they are lysed with Triton X, and the free peroxidase is then quantified by adding 2,2-azino-di-[3-ethylbenzo-thiazoline] sulfonate or ABTS marketed by Boehringer Mannheim and by measuring at 405 nm the extinction of the colored product which has been formed.

It was found that while in the presence of 1.67 $\mu$g/ml of laminarin sulphate, the cellular migration is inhibited to an extent of 50%±6%, it is not inhibited in presence of heparin at the same concentration of 1.67 $\mu$g/ml, an inhibition of only 10%±5% being obtained in the presence of 4.2 $\mu$g/ml of heparin.

The inhibiting power, depending form the dose, of laminarin sulphate with respect to the migration of the PMN being thus demonstrated, it appears that the said laminarin sulphate can be used for the prevention of the induction of the inflammatory response, the migration in question being an important step in the inflammatory process.

Test 3: Influence on the Adhesion of the Cells Induced by Selectin

The adhesion of the inflammatory cells against the wall of the blood vessels is a preliminary condition for the migration of the cells within the tissues. This is a process comprising several steps which occurs under the influence of the adhesion molecules. Under the influence of the selectins, i.e. a family of adhesion molecules, the first contacts between leukocytes and endothelium take place. The said selectins recognize the oligosaccharidic ligands of the cellular surface.

The said adhesion is labile which enables the leucocytes to move slowly along the vascular endothelium; that phenomenon is the so called "rolling" of the leucocytes.

The family of selectins comprises three representatives, i.e. the L-selectins, the P-selectins and the E-selectins; they are expressed by different cells; in that connection L-selectins are expressed by the leukocytes, P-selectins by the endothelial cells and by the blood platelets and E-Selectins are expressed by the vascular endothelial cells.

Due to the fact that the "rolling" induced by the selectins is a preliminary condition for a strong adhesion and finally for an extravasation of the inflammatory cells in the tissues, the obtention of an inhibition of that early process constitutes an interesting option for an anti-inflammatory therapy.

Consequently, the effect of laminarin sulphate has been examined through the direct quantification of the cells bond to the selectins immobilized on microplates.

Figure 3A:
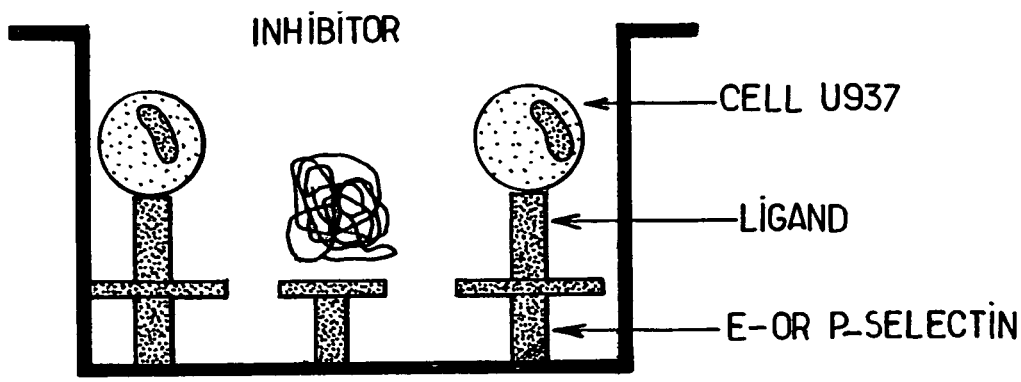
FIG. 3a and 3b respectively show the influence of laminarin sulfate on the adhesion of the cells of E-selectin or P-selectin (FIG. 3a) and of L-selectin (FIG. 3b).
Figure 3B:
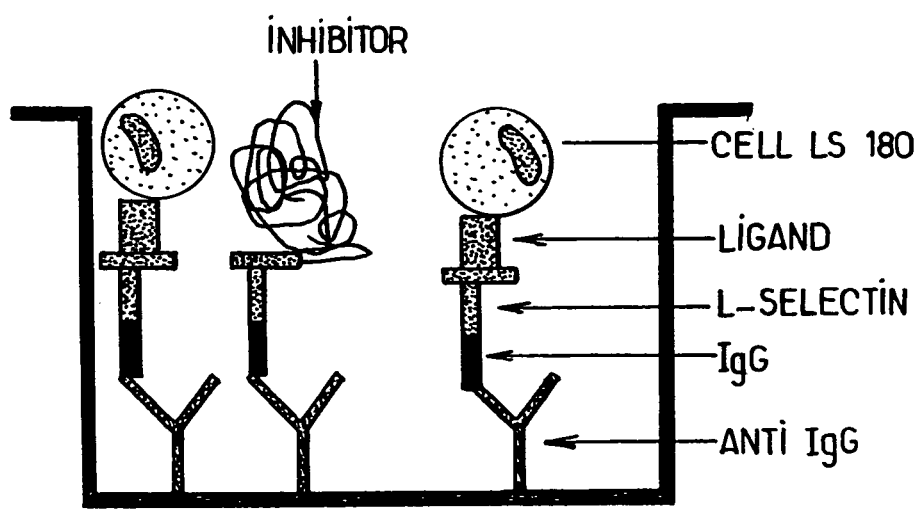

The influence of the laminarin sulphate on the adhesion of the cells due to the selectins has been studied first under static conditions as schematically shown on FIG. 3a (E-selectins or P-selectins) and 3b (L-selectins). The selectin has been deposited on a microtitration plate; in that respect and in the case of L-selectin the human chimera Fc of L-selectin has been used. Then, the plate was incubated with the test substance and with cells carrying the ligands of the corresponding selecting, that is to say in the case of L-selectin the human cellular line LS 180 of the adenocarcinoma of the colon and in the case of the selectins P and E the human lymphomic cellular line U 937.

The number of cells bond to the microtitration plate after washing and subsequent lysis of these cells was determined and their lactate dehydrogenase content was determined by way of an enzymatic reaction.

The obtained results are collected in table 1.

TABLE 1

| Tested product | Concentration in $\mu$g/ml | Inhibition expressed in % of the cellular adhesion on | |
|---|---|---|---|
| | | P-selectin | L-selectin |
| Laminarin sulphate | 5 | 50 ± 2 | 33 ± 1 |
| | 25 | 63 ± 3 | 89 ± 10 |
| Heparin | 5 | 12 ± 5 | 15 ± 5 |
| | 25 | 30 ± 4 | 32 ± 3 |

Test 4: Examination of the Anti-Coagulant Activity

Due to the fact that when using laminarin sulphate for its inflammation inhibiting activity its anti-coagulant activity might raise problems from the point of view of side effects, the influence of laminarin sulphate on coagulation has been examined.

The anti-coagulant activity which depends from the concentration of laminarin sulphate has been determined in comparison with that of heparin in the classical coagulation tests APTT or "Aktivierte partielle Thromboplastin-Zeit", of the duration of the prothrombin, by way of the test so called "HEPTEST" and the duration of the thrombin. The APTT reflects an interaction with the intrinsic system of the coagulation while the duration of prothrombin reflects an interaction with the extrinsic coagulation; the so called "HEPTEST" is a classical test for the measurement of the inhibiting activity of heparin with respect to the Xa factor and the duration of thrombin corresponds to the last step of the coagulation, i.e. the formation of fibrins induced by the thrombin. In contradiction with that of heparin, the activity of laminarin sulphate in the so called "HEPTEST" is more than 20 times weaker. Similarly and with respect to the duration of prothrombin, the laminarin sulphate has no pronounced anti-coagulant effect as in the case of heparin. The specific activity (IU/mg) in the APTT represents 30% of the activity of heparin and in the case of the duration of thrombin it represents 60%. In order to totally prevent the coagulation it is convenient to use in the case of APTT a concentration 4 times higher and in the case of the duration of thrombin a concentration 20 times higher.

In the specific anti-factor Xa and anti-thrombin tests using chromogeneous substrates, it is noticed that laminarin sulphate in contradiction with heparin does not present a significant anti-factor Xa activity dependent from anti-thrombin nor an anti-thrombin activity. The effect in the case of the duration of thrombin can be considered as being due to an inhibition of thrombin dependent from the cofactor II heparin. Due to the fact on the one hand of the weaker specific activity and, on the other hand of the profile dependent from concentration and still on the other hand of other researches related to the mechanism of action, it is possible to consider that in the case of laminarin sulphate, the bleeding risk is significantly weaker than in the case of heparin. For that reason and due to the better effect in the systems of anti-inflammatory tests, the profile "utility/risk" moves in the case of laminarin sulphate unequivocally in the sense of an anti-inflammatory effect. It follows that the anti-inflammatory properties of laminarin sulphate can be advantageously used without the apprehension of undesirable side effects on coagulation.

III—Examination In Vivo of the Anti-Inflammatory Activity of Laminarin Sulphate

The topic activity which inhibits inflammation and which is presented by laminarin sulphate, has been tested in the model constituted by the edema of the ear of the mouse induced with croton oil. The control was indomethacin. The tested animals were male mice of the type Swiss CD-1 whose weight was 20 to 25 g. Three groups of tests were carried out on three groups of animals. The first group is a negative control group wherein only the pro-inflammatory agent consisting of croton oil was used. The second group is a positive control group and comprises the use of croton oil and of indomethacin (200 nMol/ear which corresponds to 71.56 μg/ear). The third group relates to the use of laminarin sulphate and comprises the use of 70 μg of croton oil and of increasing amounts of laminarin sulphate (100, 250, 500, 750 and 1000 μg/ear).

In the case of the control groups, of the group of reference and of the group comprising the use of the different concentrations of laminarin sulphate, 10 mice were used each time. Twelve hours before the experimentation, the animals did not receive food, but received water as much as they wished. On each ear (surface of about 1 cm$^2$) 70 μg of croton oil were applied at the same time as indomethacin or laminarin sulphate or dexamethasone. Four hours later, samples having a diameter of 7 mm were cut up and weighed.

For the statistical exploitation an analysis of the variance (ANOVA) as well as the Scheffe test were carried out.

The intensity of the inhibition of inflammation expressed in percentages for different amounts of the tested products, i.e. indomethacin, dexamethasone and laminarin sulphate was evaluated. It has been noticed that a concentration of 250 μg of laminarin sulphate per ear is equipotent to 72 μg of indomethacin per ear. From the molar point of view, laminarin sulphate is at that concentration, i.e. 25 nMol, nine times more active than indomethacin at 200 nMol.

Furthermore it was possible to notice, at the end of another experience, that at the equimolar concentration of 0.12 mmol/ear, laminarin sulphate is more efficient than dexamethasone.

In a control experiment, wherein laminarin sulphate was not applied to the ear simultaneously with croton oil but after the latter, no difference from the point of view of the inhibiting activity was noticed.

It follows that a falsely or untruly positive effect due to a physical interaction with croton oil can be considered as inexisting.

In short, laminarin sulphate having a degree of sulphation higher or equal to 1.9, preferably from 2 to 2.5 and a degree of polymerization equal to that of the natural molecule, i.e. 20 to 30 and preferably from 23 to 25, has been prepared using a partial synthesis by sulphation of the laminarin extracted from brown algae which is a natural vegetal raw material particularly abundant and renewable. This new product is able to act in an inhibiting manner at various steps of the inflammation.

It inhibits the complementary activity as well in the case of an activation by the classical way as in the case of an activation by the alternative route and interacts consequently at a very early moment with the inflammatory process.

Furthermore it inhibits in the case of the granulocytes having polymorph nuclei, the chemotaxy induced by serum activated with zymosan and, by way of consequence, it is able to hinder the migration of inflammatory cells within the tissue.

Finally, laminarin sulphate prevents the bond or binding of cells to P-selectin and to L-selectin and by way of consequence the initial step of the cascade of adhesions.

The effects demonstrated in vitro relative to an inhibiting activity of the inflammation are confirmed by the marked efficiency of the said laminarin sulphate in the model of the edema of the ear of the mouse induced by croton oil. In these experiences, laminarin sulphate is more efficient than heparin. Its anti-coagulant activity is however clearly weaker than that of heparin due to which laminarin sulphate presents a ratio "profit/risk" clearly better. Furthermore, laminarin sulphate does not present any cytotoxic property even at the highest tested concentration, i.e. 100 μg/ml, no cytotoxic effect was noticed.

In order to test cytoxicity, the following cellular lines were used: MDA-MB-231 (human mammary carcinoma); MCF (human mammary carcinoma); U937—(human lymphoma); and, LS180 (human adenocarcinoma).

The test used is a 5 days proliferation test and the determination of the number of living cells was carried out by coloration with crystallin violet or crystallin purple. A 5 day proliferation test with determination of the number of living cells using the test MTT has also been carried out. Finally the acute cytotoxicity has been determined using a kit marketed by the company Boehringer Mannheim under the title "Cytotoxicity detection kit" (LDH).

As non-limitative examples but as corresponding to advantageous embodiments, the compositions of several pharmaceutical formulations, i.e. that of a cream, of a sachet, and of a solution for aerosol are hereafter indicated.

1. Composition of a Cream According to the Invention

| | |
|---|---|
| Demineralized water | 69.5% |
| Glycerin | 5.0% |
| Acrylate | 0.2% |
| Laminarin sulphate | 1.0% |
| PEG 100 stearate | 4.0% |
| Cetearylic alcohol | 2.0% |
| Preserving agent | 1.0% |
| PEG 40 stearate | 3.0% |
| Acetate of vitamin E | 0.5% |
| C12–15 alkyl benzoate | 6.5% |
| Caprylic/caprictriglycerides | 5.5% |
| NaOH | 1.8% |

2. Composition of a Sachet for Oral Administration According to the Invention

| Laminarin sulphate | 0.150 g |
|---|---|
| Saccharose | 2.850 |
| Orange aroma | Sufficient amount |

3. Composition of a Solution for Aerosol According to the Invention

| Laminarin sulphate | 1 g |
|---|---|
| Sodium chloride | 0.9 g |
| Water (for injectable preparation) | 100 ml |

The posology, especially with respect to the above said pharmaceutical forms is advantageously as follows:

In the case of the cream, 2 to 3 administrations per day are contemplated.

In the case of the sachet, 1 to 3 sachets per day for an adult person are administrated.

In the case of the aerosol, an amount of aerosol per day corresponding to an amount of active substance of 1500 to 7000 µg is administered.

The invention claimed is:

1. A method for the treatment of non-specific inflammatory disease in a patient comprising administering to the patient in need thereof a composition comprising laminarin sulfate, wherein the laminarin sulfate is sulfated to a level of at least 1.9 and the laminarin sulfate is polymerized to a degree of about 20 to about 30.

2. The method of claim 1, wherein the laminarin sulfate is sulfated to a level of about 2.0 to about 2.5.

3. The method of claim 1, wherein the laminarin sulfate is polymerized to a degree of about 23 to about 25.

4. The method of claim 1, wherein the laminarin sulfate is sulfated to a level of about 2.0 to about 2.5 and is polymerized to a degree of about 23 to about 25.

5. The method of claim 1, wherein the composition is administered locally, generally, orally, parenterally, cutaneously, subcutaneously, intraarticularly, intravenously, rectally or through the respiratory system.

6. The method of claim 1, wherein the composition is administered in a form selected from the group consisting of a tablet, a syrup, a drinkable solution, a drinkable suspension, a capsule, a hard capsule, a sachet, an injectable solution, an emulsion, an ointment, a gel, through a transdermal device, an aerosol, a suppository and a rectal injection.

7. A method according to claim 1 for the treatment in a patient of a non specific inflammatory disease through inhibition of the activation of the complement, and/or through inhibition of the chemotaxis of the inflammatory cells and/or through inhibition of the cell adhesion to the selectins L and P, the said method comprising administering to the patient in need thereof a composition comprising laminarin sulfate, wherein laminarin sulfate is sulfated to a level of at least 1.9 and wherein the laminarin sulfate is polymerized to a degree of about 20 to about 30.

8. A method for the treatment of non-specific inflammatory disease in a patient comprising administering to the patient in need thereof a composition comprising laminarin sulfate, wherein the laminarin sulfate is sulfated to a level of a least 1.9 and the laminarin sulfate is polymerized to a degree of about 20 to about 30, wherein the composition is administered orally in a tablet, syrup, drinkable solution, drinkable suspension, capsule, hard capsule or sachet.

9. A method according to claim 8 for the treatment of nonspecific inflammatory disease in a patient comprising administering to the patient in need thereof a composition comprising laminarin sulfate, wherein the laminarin sulfate is sulfated to a level of a least 1.9 and the laminarin sulfate is polymerized to a degree of about 20 to about 30, wherein the composition is administered parenterally through a subcutaneous, intra-articular or intravenous injectable solution.

10. A method according to claim 8 for the treatment of nonspecific inflammatory disease in a patient comprising administering to the patient in need thereof a composition comprising laminarin sulfate, wherein the laminarin sulfate is sulfated to a level of a least 1.9 and the laminarin sulfate is polymerized to a degree of about 20 to about 30, wherein the composition is administered cutaneously through an emulsion, ointment, gel, or transdermal device.

11. A method according to claim 8 for the treatment of non-specific inflammatory disease in a patient comprising administering to the patient in need thereof a composition comprising laminarin sulfate, wherein the laminarin sulfate is sulfated to a level of a least 1.9 and the laminarin sulfate is polymerized to a degree of about 20 to about 30, wherein the composition is administered through the respiratory system through an aerosol.

12. A method according to claim 8 for the treatment of non-specific inflammatory disease in a patient comprising administering to the patient in need thereof a composition comprising laminarin sulfate, wherein the laminarin sulfate is sulfated to a level of a least 1.9 and the laminarin sulfate is polymerized to a degree of about 20 to about 30, wherein the composition is administered rectally through a suppository or an injection.

* * * * *